United States Patent [19]
Nakamura

[11] Patent Number: 5,480,114
[45] Date of Patent: Jan. 2, 1996

[54] BIAXIAL BALANCE ADJUSTING STRUCTURE FOR MEDICAL STAND APPARATUS

[75] Inventor: Katsushige Nakamura, Hachioji, Japan

[73] Assignee: Mitaka Kohki Co., Ltd., Tokyo, Japan

[21] Appl. No.: 204,456

[22] Filed: Mar. 2, 1994

[30] Foreign Application Priority Data

Mar. 18, 1993 [JP] Japan ................................. 5-082392

[51] Int. Cl.⁶ .................................................. F16L 3/00
[52] U.S. Cl. ...................................... 248/123.2; 359/384
[58] Field of Search ........................... 248/123.1, 280.1, 248/325, 648, 665, 292.1, 281.1; 359/368, 384

[56] References Cited

U.S. PATENT DOCUMENTS

| | | | |
|---|---|---|---|
| 3,891,301 | 6/1975 | Heller | 359/384 |
| 4,339,100 | 7/1982 | Heller et al. | 248/123.1 |
| 4,344,595 | 8/1982 | Heller et al. | 248/123.1 X |
| 4,548,373 | 10/1985 | Komura | 248/280.1 X |
| 4,668,057 | 5/1987 | Kleinberg | 359/384 |
| 4,741,607 | 5/1988 | Heller | 359/384 |
| 4,881,709 | 11/1989 | Nakamura | 248/123.1 X |
| 5,205,522 | 4/1993 | Nakamura | 248/123.1 |
| 5,243,370 | 9/1993 | Slater | 248/123.1 X |

FOREIGN PATENT DOCUMENTS

2051588  3/1992  Canada.

*Primary Examiner*—Ramon O. Ramirez
*Attorney, Agent, or Firm*—Michael D. Bednarek; Marks & Murase

[57] ABSTRACT

Disclosed is a biaxial balance adjusting structure for a medical stand apparatus, containing a retaining link mechanism 4, utilizing a parallel link 2, supported on the pivot S of a frame 1; a medical optical device $W_1$ and/or auxiliary devices $W_2$, $W_3$, disposed to one end portion of the retaining link mechanism and a counterweight disposed on the other end portion thereof relative to the pivot S; characterized in that the counterweight consists of a first counterweight $W_4$ which can be moved in the horizontal direction and a second counterweight $W_5$ which can be moved in the vertical direction, and that the balance adjusting structure employs a system for moving the first and second counterweights $W_4$, $W_5$ interlocking with each other to be closer to or farther from the pivot S in the respective directions. Thus, balance adjustment in accordance with the weight change on the operating microscope side can be facilitated.

10 Claims, 5 Drawing Sheets

BIAXIAL BALANCE ADJUSTING STRUCTURE FOR MEDICAL STAND APPARATUS

BACKGROUND OF THE INVENTION

1. Field of the Invention

This invention relates to a stand apparatus, in which heavy "medical optical devices" such as an operating microscope and its auxiliary devices are supported at the front end portion of a retaining link mechanism utilizing a parallel link and are balanced with a counterweight disposed on the other end portion of the retaining link mechanism, and thus these heavy medical optical devices can be retained at the desired spatial positions during microsurgery.

2. Description of Prior Art

In the fields of eneephalotomy and eardiosurgery, a technique of so-called microsurgery is employed, in which surgeries are performed under observation of the focuses using operating microscopes. Various types of stand apparatuses, for retaining heavy operating microscope and its auxiliary devices at the desired spatial positions, to be utilized in such microsurgeries have been proposed (e.g. U.S. Pat. No. 4,339,100). These stand apparatuses generally are of a balancing structure, in which a retaining link mechanism employing a parallel link is pivotally (tiltably) supported at the middle on a :frame, and an operating microscope is supported at one end portion of the retaining link mechanism with a counterweight for countervailing the weight of the operating microscope being supported on the other end portion of the retaining link mechanism relative to the pivot thereof.

As the position where the balancing type stand apparatus is set up, an optimum position in the operating room is selected depending on the content of the surgery to be carried out, and balance adjustment is performed at the selected position. In other words, while the optimum position around the operating table is specified by a doctor prior to surgery, the doctor himself is in a sterilized region, so that the actual operations of moving the stand apparatus to the position and setting it up are carried out by a nurse who does not participate in the surgery. Since auxiliary devices such as a side microscope for assistant doctors and a video camera are attached to the operating microscope, the nurse also moves the position of the counterweight to adjust the entire balance of the stand apparatus corresponding to the weight of these devices.

However, the operation of moving such heavy counterweight is a tremendous task and is also dangerous for the nurse who is in most cases a woman. Further, the balance adjusting operation takes too much time to be advantageously rendered for emergent surgery and the like.

What is most serious in the prior art stand apparatus is that the balance adjustment between the operating microscope and the counterweight is very difficult due to the structure of the stand apparatus itself. More specifically, in order to stop the operating microscope and the auxiliary devices at the desired spatial positions, the operating microscope must be balanced in the horizontal and vertical directions. However, since the prior art stand apparatus has only one counterweight, it has not always been easy to make secured balance adjustment in the horizontal and vertical directions in accordance with the weight on the operating microscope side which changes depending on the presence or absence of various auxiliary devices by means of the single counterweight.

SUMMARY OF THE INVENTION

This invention has been accomplished noting such prior art technique and is directed to provide a biaxial balance adjusting structure for a medical stand apparatus, which enables easy and secured balance adjustment in accordance with the weight change on the operating microscope side.

In order to attain the intended object as described above, the biaxial balance adjusting structure for a medical stand apparatus according to this invention contains a retaining link mechanism, utilizing a parallel link, supported at the middle on a pivot assumed on a frame; a medical optical device and/or its auxiliary devices, disposed to one end portion of the retaining link mechanism and a counterweight disposed on the other end portion thereof relative to the pivot S; characterized in that the counterweight consists of a first counterweight which can be moved in the horizontal direction and a second counterweight which can be moved in the vertical direction, and that the balance adjusting structure employs a system for moving the first and second counterweights interlocking with each other to be closer to or farther from the pivot S in the respective directions.

When the operating microscope and other devices are to be stopped at the desired spatial positions in a medical stand apparatus employing a parallel link, the weight of the operating microscope and other devices must be balanced in the horizontal and vertical directions on each side or the pivot. Since the first counterweight and the second counterweight are designed to move closer to or farther from the pivot in the respective directions interlocking with each other, the balance adjustment both in the horizontal direction and in the vertical direction can securely and easily be carried out.

Further, the balance adjustment can more securely be carried out by allowing the ratio of the horizontal shift of the first counterweight to the vertical shift of the second counterweight to correspond to the ratio of the horizontal distance to the vertical distance as measured respectively from the pivot to the front end portion of the retaining link at which the medical optical device and/or its auxiliary devices are supported.

These and other objects of the invention together with the advantages thereof will become clearer by reading the following description referring to the attached drawings.

DESCRIPTION OF PREFERRED EMBODIMENT

Figure 1:
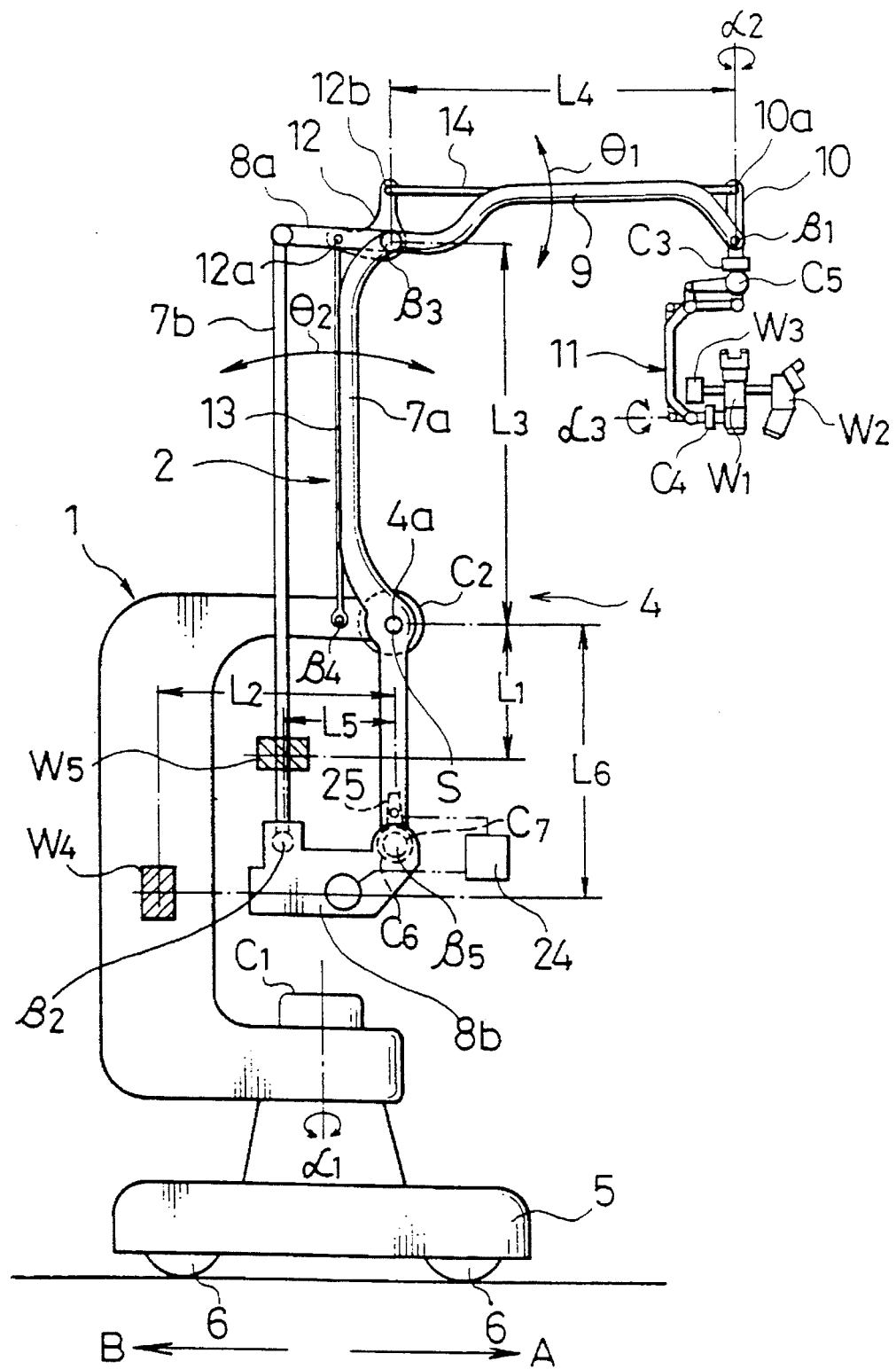
FIG. 1 shows an entire side view of the biaxial balance adjusting structure for a medical stand apparatus according to one embodiment of the invention.

A preferred embodiment of this invention will be described below referring to the attached drawings. It should be noted here that the following description is made assuming that the arrow A and the arrow B shown in FIG. 1 mean the front side and the rear side, respectively.

In the stand apparatus according to the preferred embodiment of the invention, a retaining link mechanism 4 consisting of a parallel link 2 and a supporting arm 9 is supported at a part (middle position 4a) on a pivot S assumed on a frame 1, and an operating microscope W, and other devices are supported at one end portion (connecting point $\beta_1$) of the retaining link mechanism 4, while a "counterweight" consisting of a first counterweight $W_4$ and a second counterweight $W_5$ is provided at the other end portion (connecting point $\beta_2$) of the retaining link mechanism 4. Incidentally, the expressions "one end portion" and "the other end portion" referred to in the above and the following descriptions should be understood that these expressions are made relative to the pivot S, and these two portions locate on each side of the pivot S respectively, or they locate on the opposite sides relative to the pivot S.

The base affixed with the reference number 5 has on the bottom a plurality of casters 6 with locking mechanisms, and the entire stand apparatus is designed to be able to run on the floor with the aid of these easters 6. A frame 1 having a substantially rectangular U-shaped side profile is mounted on the base 5. The frame 1 is designed to be pivotable on the vertical axis $\alpha_1$ and also to be unpivotably locked by an electromagnetic clutch $C_1$ provided on the axis $\alpha_1$.

A parallel link 2 is pivotably supported on the pivot S assumed on the upper front end side of the frame 1. The parallel link 2 is formed by combining a pair of parallel vertical arms 7a, 7b and a pair of horizontal arms 8a, 8b. Since the lower horizontal arm 8b of the parallel link 2 is of a specific structure, it will be described later. The front vertical arm 7a of the parallel link 2 is supported at the middle position 4a on the pivot S, as described above. An electromagnetic clutch $C_2$ is provided on the pivot S, so that the vertical arm 7a can be locked at a desired pivoted position (i.e. the horizontal shift $\theta_2$ of the horizontal link 2). The upper portion of the front vertical arm 7a supported on the pivot S is bulged backward so as not to interfere with the body of a doctor who performs the surgery.

The upper horizontal arm 8a of the parallel link 2 extends forward to form a supporting arm 9 integrally therewith, and a vertical front arm 10 is pivotably attached to the connecting point $\beta_1$ at the free end portion thereof. The supporting arm 9 is also bulged upward so as not to interfere with the head of the doctor. The supporting arm 9 is adapted to be shifted $\theta_1$ in the vertical direction.

A supporting parallel link 11 consisting of two parallel links which interlock with each other is provided below the front arm 10 to be pivotable on the vertical axis $\alpha_2$. An electromagnetic clutch $C_3$ is provided at the upper end of the supporting parallel link 11, and an operating microscope (medical optical device) $W_1$ which is pivotable on the axis $\alpha_3$ is attached via another electromagnetic clutch $C_4$ to the lowermost portion of the supporting parallel link 11. The supporting parallel link 11 as a whole presents a curved shape, so that the doctor can operate the operating microscope $W_1$ easily. The view angle of the operating microscope $W_1$ can be changed by transforming the supporting parallel link 11. Incidentally, the transformed state of the supporting parallel link 11 can be locked by an electromagnetic clutch $C_5$. "Auxiliary devices" such as a side microscope $W_2$ for assistant doctors and a video camera $W_3$ for recording are attached to the operating microscope $W_1$. The weight on the operating microscope ($W_1$) side changes by attaching or detaching these auxiliary devices.

A bell crank 12 is pivotably supported on the connecting point $\beta_3$ which is the origin of the supporting arm 9, and the rear end portion 12a or the bell crank 12 is connected via a vertical subarm 13 to the connecting point $\beta_4$ of the frame 1, while the upper end 12b of the bell crank 12 is connected via a horizontal subarm 14 to the upper end portion 10a of the front arm 10. In other words, on the connecting point $\beta_3$ which is the origin of the supporting arm 9 is supported the bell crank 12, having the rear end portion 12a on the horizontal line including the connecting point $\beta_3$ and the upper end portion 12b on the perpendicular line including the connecting point $\beta_3$; the rear end portion 12a of the bell crank 12 and the connecting point $\beta_4$ of the frame 1 are connected by the vertical subarm 13, which is parallel with the vertical arm 7a and has a length which is equal to the distance from the connecting point $\beta_3$ of the vertical arm 7a to the pivot S; and the upper end portion 12b of the bell crank 12 and the upper end portion 10a of the front arm 10 are connected by the horizontal subarm 14 which is parallel with the supporting arm 9 and has a length which is equal to that of the supporting arm 9.

With the aid of the vertical subarm 13 and the horizontal subarm 14 additionally provided, a "parallel link" is formed by the pivot S→connecting point $\beta_3$→ rear end portion 12a→connecting point $\beta_4$; while another "parallel link" is formed by the connecting point $\beta_3$→connecting point $\beta_1$→upper end portion 10a →upper end portion 12b. Accordingly, since the bell crank 12 cannot be turned no matter how the parallel link 2 is transformed, the front arm 10 is constantly maintained in the vertical posture, and consequently the axis $\alpha_2$ of the supporting parallel link 11 is prevented from tilting to maintain constantly the vertical posture.

Next, the structure of the lower horizontal arm 8b of the parallel link 2 will be described referring to FIGS. 3 to 7. The lower horizontal arm 8b is provided via a "mechanical section" with a first counterweight $W_4$ which can be moved in the horizontal direction and a second counterweight $W_5$ which can be moved in the vertical direction. The first counterweight $W_4$ and the second counterweight $W_5$ are substantially of the same weight.

Figure 2:
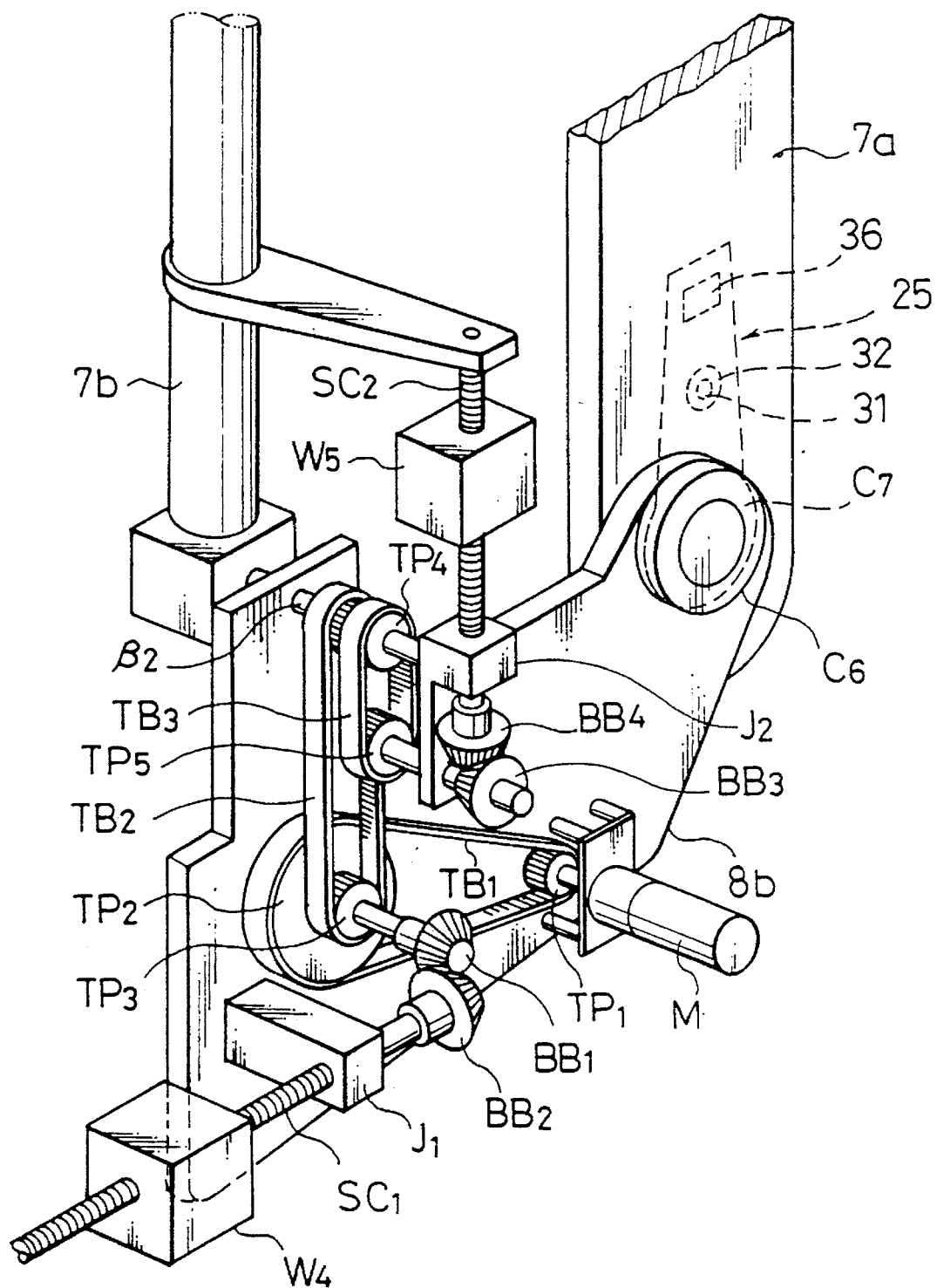
FIG. 2 shows a perspective view of a drive means.
Figure 3:
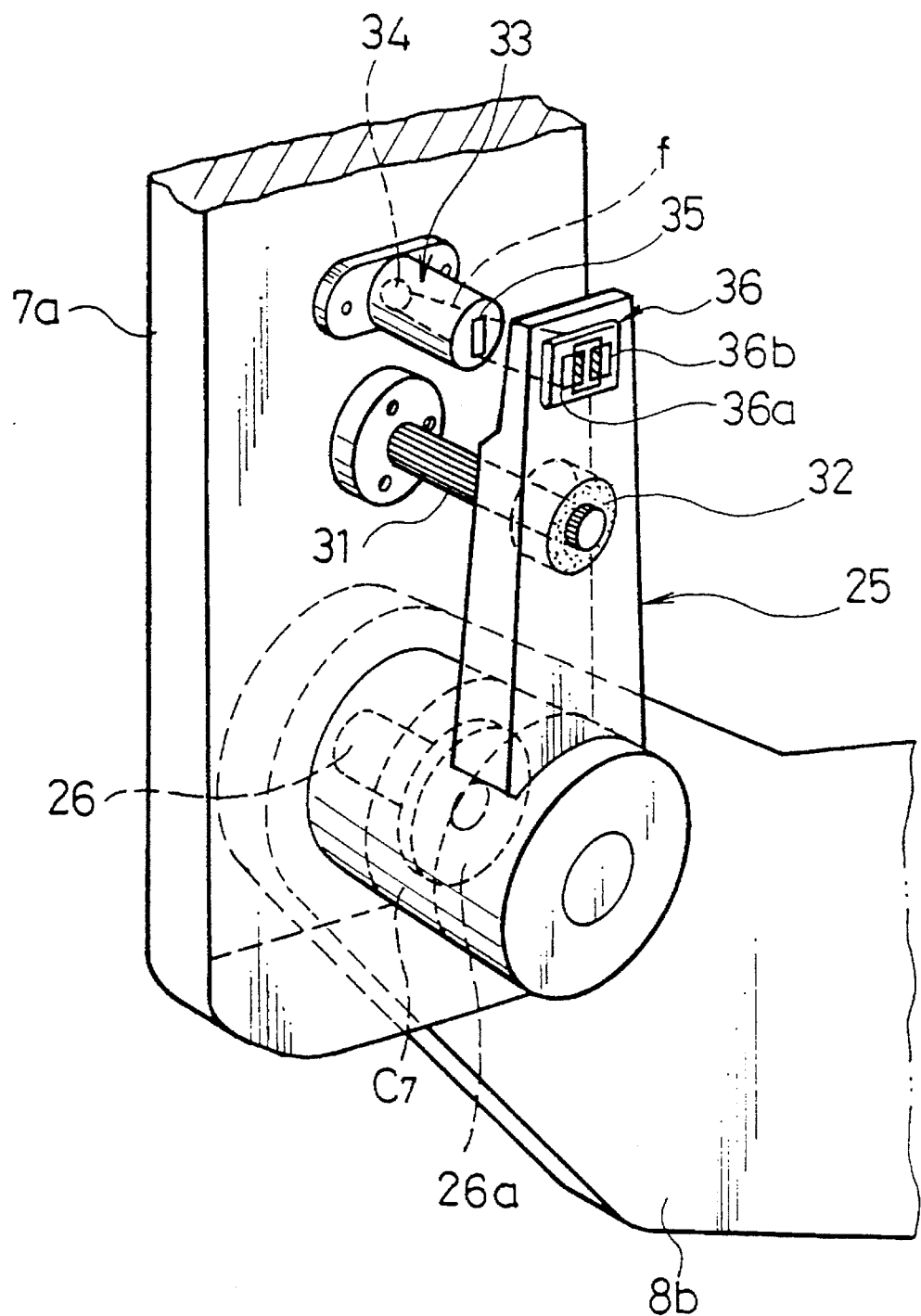
FIG. 3 shows a perspective view of a displacement detecting means.
Figure 4:
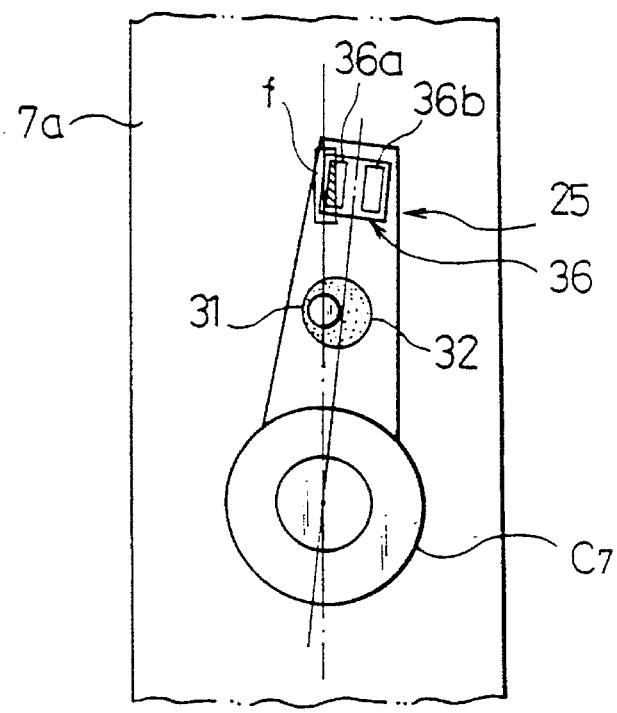
FIG. 4 shows in side view a detection lever which is shifted to one side.
Figure 5:
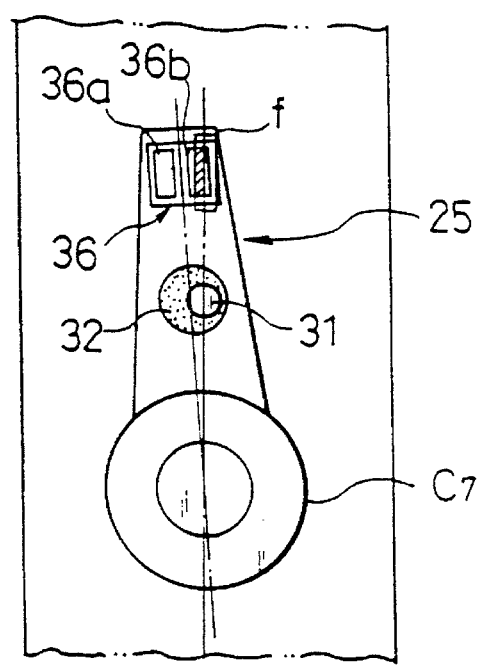
FIG. 5 shows in side view a detection lever which is shifted to the other side.
Figure 6:
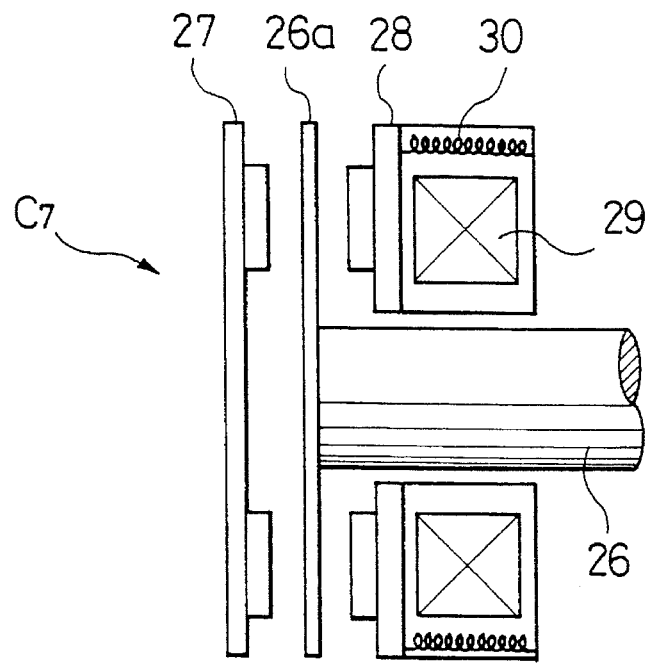
FIG. 6 shows in cross-sectional view an electromagnetic clutch assuming an unlocked state.
Figure 7:
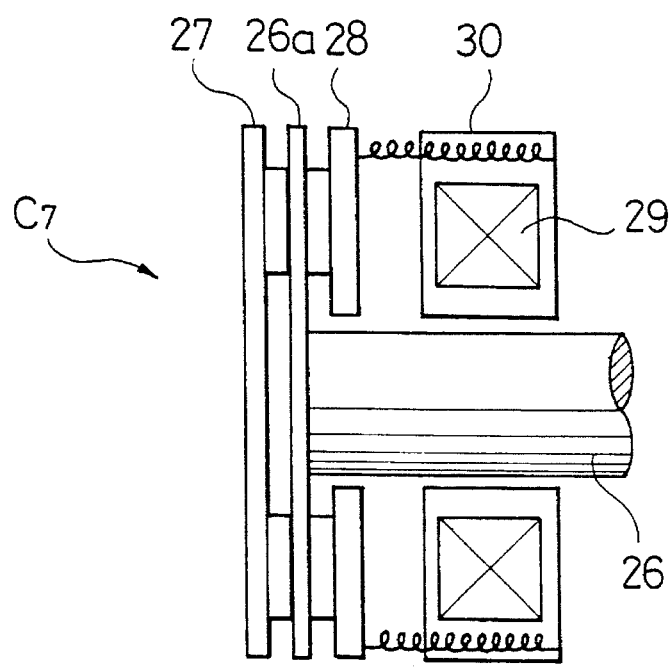
FIG. 7 shows in cross-sectional view an electromagnetic clutch assuming a locked state.

FIG. 2 shows an example of the "mechanical section" for moving the first counterweight $W_4$ and the second counterweight $W_5$. To describe more specifically, a motor M is mounted on the lower horizontal arm 8b, and the torque of a timing pulley $TP_1$ to be rotated by the motor M is transmitted by a timing belt $TB_1$ to a timing pulley $TP_2$ having a larger diameter. The larger-diameter timing pulley $TP_2$ is provided with a smaller-diameter timing pulley $TP_3$ and a bevel gear $BB_1$ coaxially therewith. The bevel gear $BB_1$ is engaged with a bevel gear $BB_2$ provided at one end portion of a screw $SC_1$ retained horizontally by a bearing $J_1$. The first counterweight $W_4$ is shiftably engaged with the screw $SC_1$. Meanwhile, the torque of the timing pulley $TP_2$ is transmitted via a timing belt $TB_2$ to a timing pulley $TP_4$, and the torque of the timing pulley $TP_4$ is transmitted via another timing belt $TB_3$ to a timing pulley $TB_5$ to rotate a bevel gear $BB_3$. A counter bevel gear $BB_4$ is engaged with the bevel gear $BB_3$, and a screw $SC_2$ supported vertically by a bearing $J_2$ is rotated thereby. The second counterweight $W_5$ is shiftably engaged with the screw $SC_2$. If the motor M in the "mechanical section" of the structure as described above is driven in one direction, the first counterweight $W_4$ is shifted leftward in FIG. 2, and the second counterweight $W_5$ is shifted downward in FIG. 2. Both the horizontal (leftward) shift of the first counterweight $W_4$ and the vertical (downward) shift of the second counterweight $W_5$, when considered relative to the pivot S, are "directing farther from the pivot S" in the respective directions. On the other hand, if the motor M is driven in the reverse direction, the first counterweight $W_4$ is shifted rightward in FIG. 2, and the second counterweight $W_5$ is shifted upward in FIG. 2. The shift of the first counterweight $W_4$ and that of the second counterweight $W_5$ are "directing closer to the pivot S" in the respective directions. The motor M is connected to a control section 24 (see FIG. 1) which outputs commands on the rotational direction and rotational amount, and the control section 24 and the motor M constitute a "drive means". It should be noted here that the ratio of the number of teeth in the timing pulley $TP_3$ to that in the timing pulley $TP_4$ in the "mechanical section" is allowed to correspond to the ratio of the horizontal distance $L_4$ to the vertical distance $L_3$, as measured respectively from the pivot S to the connecting point $\beta_1$. Namely, the number of teeth in the timing pulley TP3 and that in the timing pulley $TP_4$ are set in such a way that the ratio of the horizontal shift of the first counterweight $W_4$ to the vertical shift of the second counterweight $W_5$ which are moved by the driving of the motor M may correspond to $L_4:L_3$.

Next, a detection lever 25 is provided on the left side (reverse side in FIG. 1) or the connecting point $\beta_5$ where the front vertical arm 7a and the lower horizontal arm 8b are connected. While a conventional electromagnetic clutch $C_5$ is disposed on the right side of the connecting point $\beta_5$, the detection lever 25 is attached to another electromagnetic clutch $C_7$ disposed to a connecting shaft 26 (see FIG. 3) penetrating the lower horizontal arm 8b ("which is a counterpart member") through the front vertical arm 7a. More specifically, a disc-shaped flange 26a is formed at one end of the connecting shaft 26, and the electromagnetic clutch $C_7$ is provided with a fixed flange 27 and a movable flange 28. The flange 26a is grasped and locked between the fixed flange 27 and the movable flange 28. The movable flange 28 is provided with an electromagnetic coil 29 on which the movable flange 28 is magnetically adsorbed and a spring 30 which urges the movable flange 28 toward the fixed flange 27. Accordingly, the electromagnetic coil 29 attracts the movable flange 28 overcoming the force of the spring 30 during energization, so that the detection lever 25 assumes a state of free rotation with respect to the connecting shaft 26 (see FIG. 6). However, the attraction by the electromagnetic coil 29 is not exerted during deenergization, so that the movable flange 28 is pushed toward the fixed flange 27 to hold the flange 26a of the connecting shaft 26 between the fixed flange 27 and the movable flange 28, and thus the detection lever 25 can be turned integrally with the connecting shaft 26 (see FIG. 7).

A metal shaft 31 is disposed to protrude from the vertical arm 7a at a position opposing to the detection lever 25, and the outer end portion of the shaft 31 is resiliently supported by a resilient bushing 32 disposed in the middle of the detection lever 25. An irradiation section 33 for irradiating a beam f is provided on the vertical arm 7a at a position opposing to the upper end portion of the detection lever 25. The irradiation section 33 contains a light-emitting diode 34 therein, and the beam f from the light-emitting diode 34 is designed to pass through a slit 35 (FIG. 3) and impinge upon the upper end portion of the detection lever 25. The upper end portion of the detection lever 25 to be irradiated with the beam f is provided with a two-piece photo-location section 36 having two sensors 36a,36b. Accordingly, so long as the detection lever 25 is maintaining a vertical neutral position relative to the vertical arm 7a, the beam f transmitted through the slit 35 impinges at the middle of the two sensors 36a,36b, and thus the sensors 36a,36b receive the beam f on the same area, producing no output difference. However, if the detection lever 25 is pivoted to either side and deviated from the neutral position, the photo-detecting area in the sensor 36a or 36b locating on the side opposite to the side the detection lever 25 is shifted is increased to generate an output difference, thus enabling detection of the shift. The photo-location section 36 is electrically connected to the control section 24, and the control section 24 allows the motor M to be driven based on the signal from the photo-location section 36, whereby the first counterweight $W_4$ and the second counterweight $W_5$ can be moved in a direction such that the detection lever 25 can resume the neutral position. The detection lever 25, the irradiation section 33, the photo-location section 36, etc. constitute the "displacement detection means".

In the meantime, the operational procedures of the stand apparatus will now be described. First, the entire stand apparatus is carried to a position near the operating table specified by a doctor. A specified side microscope $W_2$ and a video camera $W_3$ are attached to the operating microscope $W_1$. At this point, the weight of the counterweights $W_4,W_5$ and the weight on the operating microscope ($W_1$) side including the side microscope $W_2$ and the video camera $W_3$ (hereinafter referred to as "operating microscope, etc. $W_{1-3}$") are not necessarily balanced. Incidentally, the retaining link mechanism 4 itself from which the counterweights $W_4,W_5$ and the operating microscope, etc. $W_{1-3}$ are detached is balanced on the pivot S.

Subsequently, the retaining link mechanism 4 is once allowed to resume the standard posture as shown in FIG. 1, and the electromagnetic clutch $C_7$ is actuated to immobilize the detection lever 25 onto the connecting shaft 26 of the lower horizontal arm 8b. If the weight of the operating microscope, etc. $W_{1-3}$ and that of the counterweights $W_4,W_5$ in this state is not balanced, the angle of the front vertical arm 7a is inevitably changed with respect to the lower horizontal arm 8b which is a "counterpart member", so that the detection lever 25 locked integrally with the connecting shaft 26 of the lower horizontal arm 8b is pivoted or shifted relative to the vertical arm 7a.

Since the detection lever 25 and the vertical arm 7a constitute via the resilient bushing 32 a resilient supporting structure, the detection lever 25 has an allowance of being shifted within the maximum elastic deformation range of the resilient bushing 32. When the detection lever 25 is shifted relative to the vertical arm 7a, the light receiving area receiving the beam f from the irradiation section 33 in the sensor 36a or 36b locating on the side opposite to the direction the detection lever 25 is shifted is increased to cause an output difference in the photo-location section 36, and thus the direction that the detection lever 25 is shifted, i.e. the change in the angle of the vertical arm 7a with respect to the lower horizontal arm 8b which is a "counterpart member" at the connecting point $\beta_5$ can be found.

Accordingly, the control section 24, upon receipt of a signal from the photolocation section 36, decides the rotational direction of the motor M to drive the motor M in the direction and in an amount necessary to correct the displacement of the detection lever 25, whereby the first counterweight $W_4$ and the second counterweight $W_5$ are moved. In other words, if the weight of the operating microscope, etc. $W_{1-3}$ is large, the first counterweight $W_4$ and the second counterweight $W_5$ are moved in the horizontal direction and in the vertical direction, respectively, to be spaced farther from the pivot S; whereas if the weight of the operating microscope, etc. $W_{1-3}$ is small, the first counterweight $W_4$ and the second counterweight $W_5$ are moved in the horizontal direction and in the vertical direction, respectively, to be closer to the pivot S. Besides, the ratio of the shift of the first counterweight $W_4$ to the shift or the second counterweight $W_5$ in the direction to be spaced from or closer to the pivot S is allowed to correspond to $L_4:L_3$, as described above.

Thus, the reason why the weight of the operating microscope, etc. $W_{1-3}$ can be balanced by moving the first counterweight $W_4$ and the second counterweight $W_5$ will be described below. In such type of stand apparatus, the weight of the operating microscope, etc. $W_{1-3}$ and that of the first and second counterweights $W_4$, $W_5$ must be balanced in the horizontal direction and in the vertical direction on the pivot S. Namely, to describe referring to FIG. 1, while the weight of the operating microscope, etc. $W_{1-3}$ and the weight of the counterweights $W_4, W_5$ must satisfy the following relationship:

* Balance $\theta_1$ in the vertical direction:

$$W_{1-3} \times L_3 = (W_4 \times L_6) + (W_5 \times L_1)$$

* Balance $\theta_2$ in the vertical direction:

$$W_{1-3} \times L_4 = (W_4 \times L_2) + (W_5 \times L_5),$$

the entire balance adjustment of the operating microscope, etc. $W_{1-3}$ on the pivot S can securely be achieved, because they are balanced with the first counterweight $W_4$ and the second counterweight $W_5$ in the respective directions.

After the balance adjustment is thus achieved and the first counterweight $W_4$ and the second counterweight $W_5$ are moved to the respective balancing points, the displacement of the detection lever 25 is corrected to allow the detection lever 25 to resume the neutral position. The photo-location section 36 detects this state, and the control section 24 stops driving of the motor M to allow the first counterweight $W_4$ and the second counterweight $W_5$ to stop at the respective points. Now that the balance adjustment between the weight of the operating microscope, etc. $W_{1-3}$ and that of the counterweights $W_4, W_5$ is completed, the electromagnetic clutch $C_7$ of the detection lever 25 is deactuated to provide a free joint at the connecting point $\beta_5$ connecting the vertical arm 7a and the lower horizontal arm 8b, before use.

Meanwhile, the bell crank 12, the vertical subarm 13, the horizontal subarm 14 and the front arm 10 disposed in the embodiment described above constitute a structure where the supporting parallel link 11 for supporting the operating microscope, etc. $W_{1-3}$ can constantly maintain the vertical posture, even if the operating microscope, etc. $W_{1-3}$ are moved in the horizontal and vertical directions. In this regard also, the structure of the embodiment facilitates the balancing operation.

Further, while the frame 1 described in the above embodiment is of a floor type which is set on the floor, the frame 1 may be of a ceiling type which is suspended from the ceiling of the operating room.

Meanwhile, the technique of detecting displacement of the retaining link mechanism 4 may not be limited to the embodiment utilizing the detection lever 25 as described above, and other means such as rotary encoders can be utilized. Further, the position where the displacement is detected may not be limited to the connecting point $\beta_5$.

In addition, the "auxiliary devices" may not be limited to the side microscope $W_2$ and video camera $W_3$, and other devices can be attached.

The constitution of the biaxial balance adjusting structure for a medical stand apparatus according to this invention is as described above, and the first counterweight and the second counterweight are designed to be moved in the horizontal and vertical directions, respectively, closer to or farther from the pivot interlocking with each other, whereby the balance adjustment of the operating microscope and other devices both in the horizontal direction and in the vertical direction can securely and easily be achieved.

What is claimed is:

1. A biaxial balance adjusting structure for a medical stand apparatus, comprising:

a retaining link mechanism, utilizing a parallel link, supported at the middle on a pivot assumed on a frame;

a medical optical device and/or its auxiliary devices, disposed to one end portion of said retaining link mechanism; and a counterweight disposed on the other end portion of said retaining link mechanism relative to the pivot;

wherein said counterweight consists of a first counterweight which can be moved in the horizontal direction and a second counterweight which can be moved in the vertical direction, and said first and second counterweights are interlocked with each other so that they can simultaneously be moved closer to or farther from the pivot in the respective directions.

2. The biaxial balance adjusting structure for a medical stand apparatus according to claim 1, wherein said parallel link is formed by combining a pair of parallel vertical arms and a pair of parallel horizontal arms comprising an upper horizontal arm and a lower horizontal arm, one of said vertical arms being supported at the middle on the pivot assumed on said frame; wherein said parallel link and a supporting arm are formed to extend to one side from the upper horizontal arm of said parallel link thereby forming a retaining link mechanism, with a medical optical device and/or its auxiliary devices being attached to the one end portion of said retaining link mechanism; and wherein said first counterweight and said second counterweight are supported by said lower arm of said parallel link.

3. The biaxial balance adjusting structure for a medical stand apparatus according to claim 2, further comprising a displacement detection means for detecting the pivoting shift of a detection lever with respect to said vertical arms, said displacement detecting means comprising:

a shaft connecting said detection lever and one of said vertical arms;

an electromagnetic clutch pivotably supporting said detection lever;

a resilient bushing supporting one end of said detection lever; and a beam irradiation section provided on one of said detection lever and the vertical arm connected to said shaft, and a photo location section provided on the other of said detection lever and the vertical arm connected to said shaft.

4. The biaxial balance adjusting structure for a medical stand apparatus according to claim 3, further comprising:

a drive means for moving said first and second counterweights in respective horizontal and vertical directions, said drive means including a mechanical section for shifting said first counterweight and said second counterweight simultaneously in respective horizontal and vertical directions;

a motor for driving said mechanical section; and a control section for controlling said motor in accordance with an output from the photo-location section.

5. The biaxial balance adjusting structure for a medical stand apparatus according to claim 3, wherein said retaining link mechanism further comprises:

a vertical subarm disposed in parallel relation to one of said vertical arms, said vertical subarm having a length substantially equal to the vertical displacement from said pivot to an upper end portion of one of said vertical arms;

a bell crank connected to said parallel link and, at a first point, to an upper end portion of said vertical subarm;

a supporting arm connected at one end to said parallel link and supporting said medical optical device and/or its auxiliary devices at another end;

a horizontal subarm disposed in parallel relation to said supporting arm and having a substantially equal length as said supporting arm, said horizontal subarm being connected at a second point to an upper portion of said bell crank.

6. The biaxial balance adjusting structure for a medical stand apparatus comprising:

a retaining link mechanism, utilizing a parallel link, supported at the middle on a pivot assumed on a frame;

a medical optical device and/or its auxiliary devices, disposed to one end portion of said retaining link mechanism; and a counterweight disposed on the other end portion of said retaining link mechanism relative to the pivot;

wherein said counterweight consists of a first counterweight which can be moved in the horizontal direction and a second counterweight which can be moved in the vertical direction, and said first and second counterweights are interlocked with each other so that they can simultaneously be moved closer to or farther from the pivot in the respective directions;

wherein the ratio of the horizontal shift of said first counterweight to the vertical shift of said second counterweight corresponds to the ratio of the horizontal distance to the vertical distance as measured respectively from the pivot to the one end portion of said retaining link mechanism at which said medical optical device and/or its auxiliary devices are supported.

7. The biaxial balance adjusting structure for a medical stand apparatus according to claim 6, wherein said parallel link is formed by combining a pair of parallel vertical arms and a pair of parallel horizontal arms comprising an upper horizontal arm and a lower horizontal arm, one of said vertical arms being supported at the middle on the pivot assumed on said frame; wherein said parallel link and a supporting arm are formed to extend to one side from the upper horizontal arm of said parallel link thereby forming a retaining link mechanism, with a medical optical device and/or its auxiliary devices being attached to the one end portion of said retaining link mechanism; and wherein said first counterweight and said second counterweight are supported by said lower arm of said parallel link.

8. The biaxial balance adjusting structure for a medical stand apparatus according to claim 7, further comprising a displacement detection means for detecting the pivoting shift of a detection lever with respect to said vertical arms, said displacement detecting means comprising:

a shaft connecting said detection lever and one of said vertical arms;

an electromagnetic clutch pivotably supporting said detection lever;

a resilient bushing supporting one end of said detection lever; and a beam irradiation section provided on one of said detection lever and the vertical arm connected to said shaft, and a photo location section provided on the other of said detection lever and the vertical arm connected to said shaft.

9. The biaxial balance adjusting structure for a medical stand apparatus according to claim 8, further comprising:

a drive means for moving said first and second counterweights in respective horizontal and vertical directions, said drive means including a mechanical section for shifting said first counterweight and said second counterweight simultaneously in respective horizontal and vertical directions;

a motor for driving said mechanical section; and a control section for controlling said motor in accordance with an output from the photo-location section.

10. The biaxial balance adjusting structure for a medical stand apparatus according to claim 8, wherein said retaining link mechanism further comprises:

a vertical subarm disposed in parallel relation to one of said vertical arms, said vertical subarm having a length substantially equal to the vertical displacement from said pivot to an upper end portion of one of said vertical arms;

a bell crank connected to said parallel link and, at a first point, to an upper end portion of said vertical subarm;

a supporting arm connected at one end to said parallel link and supporting said medical optical device and/or its auxiliary devices at another end;

a horizontal subarm disposed in parallel relation to said supporting arm and having a substantially equal length as said supporting arm, said horizontal subarm being connected at a second point to an upper portion of said bell crank.

* * * * *